(12) United States Patent
Heese

(10) Patent No.: US 9,873,004 B2
(45) Date of Patent: Jan. 23, 2018

(54) SYSTEMS FOR EFFICIENT DAILY CONSTANCY CHECK OF PROTON THERAPY SYSTEMS

(71) Applicant: Varian Medical Systems Particle Therapy GmbH, Troisdorf (DE)

(72) Inventor: Juergen Heese, Cologne (DE)

(73) Assignee: Varian Medical Systems Particle Therapy GMBH, Troisdorf (DE)

( * ) Notice: Subject to any disclaimer, the term of this patent is extended or adjusted under 35 U.S.C. 154(b) by 0 days.

(21) Appl. No.: 15/492,912

(22) Filed: Apr. 20, 2017

(65) Prior Publication Data

US 2017/0216630 A1    Aug. 3, 2017

Related U.S. Application Data

(62) Division of application No. 13/238,536, filed on Sep. 21, 2011, now Pat. No. 9,645,255.

(51) Int. Cl.
*A61N 5/10* (2006.01)
*G01T 1/185* (2006.01)

(52) U.S. Cl.
CPC ............ *A61N 5/1075* (2013.01); *G01T 1/185* (2013.01); *A61N 2005/1087* (2013.01)

(58) Field of Classification Search
CPC .......... A61N 5/1075; A61N 2005/1087; G01T 1/185
USPC ....................................................... 250/374
See application file for complete search history.

(56) References Cited

U.S. PATENT DOCUMENTS

| 4,988,866 | A | 1/1991 | Westerlund |
| 5,214,578 | A | 5/1993 | Cornuejols et al. |
| 5,774,519 | A | 6/1998 | Lindstrom et al. |
| 6,225,622 | B1 | 5/2001 | Navarro |
| 6,597,005 | B1 | 7/2003 | Badura et al. |
| 2005/0006591 | A1* | 1/2005 | Virtanen ................. G01T 1/185 250/374 |
| 2008/0217561 | A1* | 9/2008 | MacKie .............. A61N 5/1048 250/492.3 |
| 2010/0066372 | A1 | 3/2010 | Breuer et al. |
| 2010/0090118 | A1* | 4/2010 | Rozenfeld ............... G01T 1/026 250/370.07 |
| 2015/0168563 | A1* | 6/2015 | Lee ...................... A61N 5/1075 250/393 |
| 2015/0352376 | A1* | 12/2015 | Wiggers ............... A61N 5/1075 250/252.1 |

(Continued)

*Primary Examiner* — David Porta
*Assistant Examiner* — Gisselle Gutierrez

(57) ABSTRACT

Systems and methods are provided for efficiently performing daily maintenance or quality assurance on proton therapy systems. Specifically, a system is provided which includes a solid-state phantom, a plurality of ionization chambers disposed within the solid-state phantom, and a measuring device coupled to the plurality of ionization chambers and operable to perform radiation measurements of proton beams received within the plurality of ionization chambers. Measurements of proton beams received in the ionization chambers may be used to derive the dose at the ionization chambers and be subsequently compared to pre-generated target data (e.g., data corresponding to proper treatment according to a radiation therapy treatment plan). If the data obtained through the maintenance procedure does not conform to the target data, the proton beam generator may be further calibrated.

13 Claims, 7 Drawing Sheets

(56) References Cited

U.S. PATENT DOCUMENTS

2016/0327659 A1* 11/2016 Shin .................... A61N 5/1075

* cited by examiner

SYSTEMS FOR EFFICIENT DAILY CONSTANCY CHECK OF PROTON THERAPY SYSTEMS

CLAIM OF PRIORITY

This application is a divisional of U.S. utility patent application Ser. No. 13/238,536, filed Sep. 21, 2011, to Juergen Heese and entitled "Method for Efficient Daily Constancy Check or Calibration of Proton Therapy System," now U.S. Patent No. 9,645,255, which is incorporated by reference herein in its entirety.

TECHNICAL BACKGROUND

Radiation therapy (RT) is a popular and efficient method for cancer treatment, where ionizing radiation is used in an attempt to destroy malignant tumor cells or to slow down their growth. RT is often combined with surgery, chemotherapy, or hormone therapy, but may also be used as a primary therapy mode. Radiation therapy may be administered as internal RT, brachytherapy or, more commonly, external beam RT.

External beam RT typically involves directing beams of radiated particles produced by sources located externally with respect to the patient or subject to the afflicted treatment area. The beam can consist of photons, electrons, protons or other heavy ions. Malignant cells are damaged by the ionizing radiation used during the RT. However, the damage from the radiation is not limited to malignant cells and thus, the dosage of radiation to healthy tissues outside the treatment volume is ideally minimized to avoid being collaterally damaged.

Proton therapy is one type of external beam radiation therapy, and is characterized for using a beam of protons to irradiate diseased tissue. The chief advantage of proton therapy over other particle-based therapies is the ability to more precisely localize the radiation dosage when compared with other types of external beam radiotherapy. During proton therapy treatment, a particle accelerator, such as a cyclotron, is used to generate a beam of protons which is subsequently directed at a tumor or target region. As the beam travels through matter (e.g., the subject), energy from the ionizing radiation is deposited along the path in the surrounding matter. This energy is known as "dose," and is used to measure the efficacy and accuracy of a radiation beam. Conventional particle accelerators used for proton therapy typically produce protons with energies in the range of 70 to 250 MeV (Mega-electron Volts: million electron Volts). As with other radiation therapies, the charged particles in proton therapy damage the DNA of cells, ultimately causing their death or interfering with their ability to reproduce. Cancerous cells, because of their high rate of division and their reduced ability to repair damaged DNA, are particularly vulnerable to attack on their DNA.

Due to their relatively large mass, proton beams typically will have commensurately less lateral side scatter in the tissue. All protons of a given energy will operate according to a certain range; and relatively few protons will travel (i.e., penetrate) beyond that distance. In addition, the radiation dose delivered to the tissue at a proton beam's target is at its apex during the last few millimeters of the particle's range—this maximum is referred to as the Bragg peak. To treat tumors at greater depths, the proton accelerator must produce a beam with higher energy, typically represented in electron volts (eV). Tumors closer to the surface of the body are treated using protons with lower energy. Thus, damage from the proton beam may be localized to malignant cells by adjusting the energy of the protons during application of treatment.

The purpose of traditional RT treatment planning methodologies is to devise a treatment regimen which produces as uniform a dose distribution as possible to the target volumes whilst minimizing the dosage outside this volume. It is crucial to successful radiation therapy that the discrepancies between dose distributions calculated at the treatment planning stage and those delivered to the patient are minimized. Moreover, just as calculating precise levels of radiation at the treatment planning stage is of great importance, naturally, so is the success of the application of radiation treatments according to the treatment plans. Discrepancies between planned treatment dosages and actually administered treatment dosages can lead to unexpected and potentially disastrous results. Accordingly, proper calibration and (ideally daily) maintenance and quality assurance of the treatment environment, and of the generated radiation beam itself is extremely vital.

Conventional maintenance or quality assurance procedures often include tests to determine a proton beam's range, and constancy. A typical range test may comprise, for example, directing a proton beam according to a treatment plan into an artificial target known as a phantom. Typically, these phantoms are implemented as plastic or glass tanks containing water with submerged or partially submerged radiation measurement devices. The phantom is mounted in one or more positions which occupy the iso-center(s) of the proton beam according to a radiation treatment plan. A proton beam is generated in a particle accelerator according to the pre-determined treatment plan and received in the radiation measurement devices which is scanned while receiving the proton beam to record the beam's characteristics (e.g., energy). Once the beam's characteristics are recorded, the beam may be calculated and compared to the treatment plan to determine congruency or a lack thereof. The proton beam generator may be subsequently re-calibrated to eliminate or mitigate any identified discrepancies between the planned beam and the actual tested beam.

Unfortunately, conventional range determination procedures may require liquid-state phantoms to be quite large. Naturally, due to the volume of liquid required, the phantoms (particularly when filled) may be cumbersome, heavy and/or physically difficult to move and adjust, often requiring two or more operators just to setup the procedure. In addition, such maintenance procedures may require significant time to refill and drain each phantom before and after use. Since these procedures must (ideally) be performed prior to the actual application of radiation treatment, in circumstances where treatments are administered with great frequency, the additional time, effort and personnel required to even attempt to perform such maintenance procedures can become quite prohibitive to conduct efficiently.

Another procedure commonly performed during daily clinical maintenance and quality assurance tests include constancy tests which measure the flux of a field of radiation generated by a proton beam. A typical constancy check includes measuring the field of radiation for a plurality of data points using a device with high spatial resolution, such as a film. However, using a medium or device having a high spatial resolution requires processing for each data point. For devices with high spatial resolution, this can be an extremely time intensive practice, especially when coupled with the performance of inefficient range detection procedures. Moreover, a single layer of film is not reusable, and repositioning multiple layers of film can be time-consuming, especially for frequent or daily tests.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

A system is provided for efficiently performing daily maintenance or quality assurance on proton therapy systems. Specifically, the system enables performance of a quick and simple daily quality assurance and maintenance procedure for proton therapy systems. The system includes a solid-state phantom, a plurality of ionization chambers disposed within the solid-state phantom, and a measuring device coupled to the plurality of ionization chambers and operable to perform radiation measurements of proton beams received within the plurality of ionization chambers. Measurements of proton beams received in the ionization chambers may be used to derive the dose at the ionization chambers and be subsequently compared to pre-generated target data (e.g., data corresponding to proper treatment according to a radiation therapy treatment plan). If the data obtained through the maintenance procedure does not conform to the target data, the proton beam generator may be further calibrated.

According to one embodiment, the solid state phantom may be composed of a plastic or similar, relatively lightweight material, and may be constructed to be of only a few centimeters in depth, thereby allowing easier mobility and adjustment, without requiring multiple operators or a water source and drain facilities. This novel system allows the performance of daily maintenance procedures to be performed which are insensitive to exact alignment of the phantom with respect to the ionization chambers, as well as makes use of the distal falloff of the Bragg peak of the proton beam by positioning an ionization chamber in the location of the distal falloff, thereby allowing the identification of small drifts in the beam's energy and therefore, efficient calculation of the range of a particle beam.

According to another aspect, a method is provided to perform constancy checks of a scanning system during daily maintenance of a proton beam spot scanning treatment system with a low resolution measurement device or medium. According to one embodiment, a proton beam is applied to a plurality of positions (e.g., a single beam may be magnetically re-directed to a plurality of spots) according to a spot scanning treatment plan. The beam is received in a re-usable, two dimensional array of regularly spaced ionization chambers at a low density. Having a lower spatial resolution arrangement allows a reduced processing time, and may be re-positioned and re-used quickly and easily.

According to yet another aspect, a method for calibrating a treatment planning system for a proton spot scanning beam delivery system is provided. In contrast to conventional proton therapy systems wherein dose delivery calculated by the treatment planning system must be adjusted for a given plan via output factors, this novel method allows a full calibration of a treatment planning system for proton beam spot scanning for all treatment plans without the need to use output factors. Calibration may be performed by measuring a homogenous radiation field generated by a proton beam in a simple, yet precise procedure involving a solid-state phantom with a single thimble ionization chamber disposed in the phantom at a shallow depth. During the testing procedure, the phantom (and ionization chamber) is placed at the iso-center of the treatment beam, where it receives a proton beam and generates a radiation field from the beam. The field is measured and, given supplied data in the form of number of radiation treatment spots, spot distances and monitor units per spot, a dose of the field may be calculated. The calculated dose can be subsequently compared to the intended dose according to a treatment plan. Unlike conventional, fluence-based calibrations, the dose to monitor unit calibrations according to embodiments are not energy dependent, thereby reducing the complexity and uncertainty of such a maintenance procedure.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Portions of the detailed description that follows are presented and discussed in terms of a method. Although steps and sequencing thereof are disclosed in figures herein (e.g., FIGS. 5, 6, and 7) describing the operations of this method, such steps and sequencing are exemplary. Embodiments are well suited to performing various other steps or variations of the steps recited in the flowchart of the figure herein, and in a sequence other than that depicted and described herein.

Conventional Liquid-State Phantoms

Figure 1:
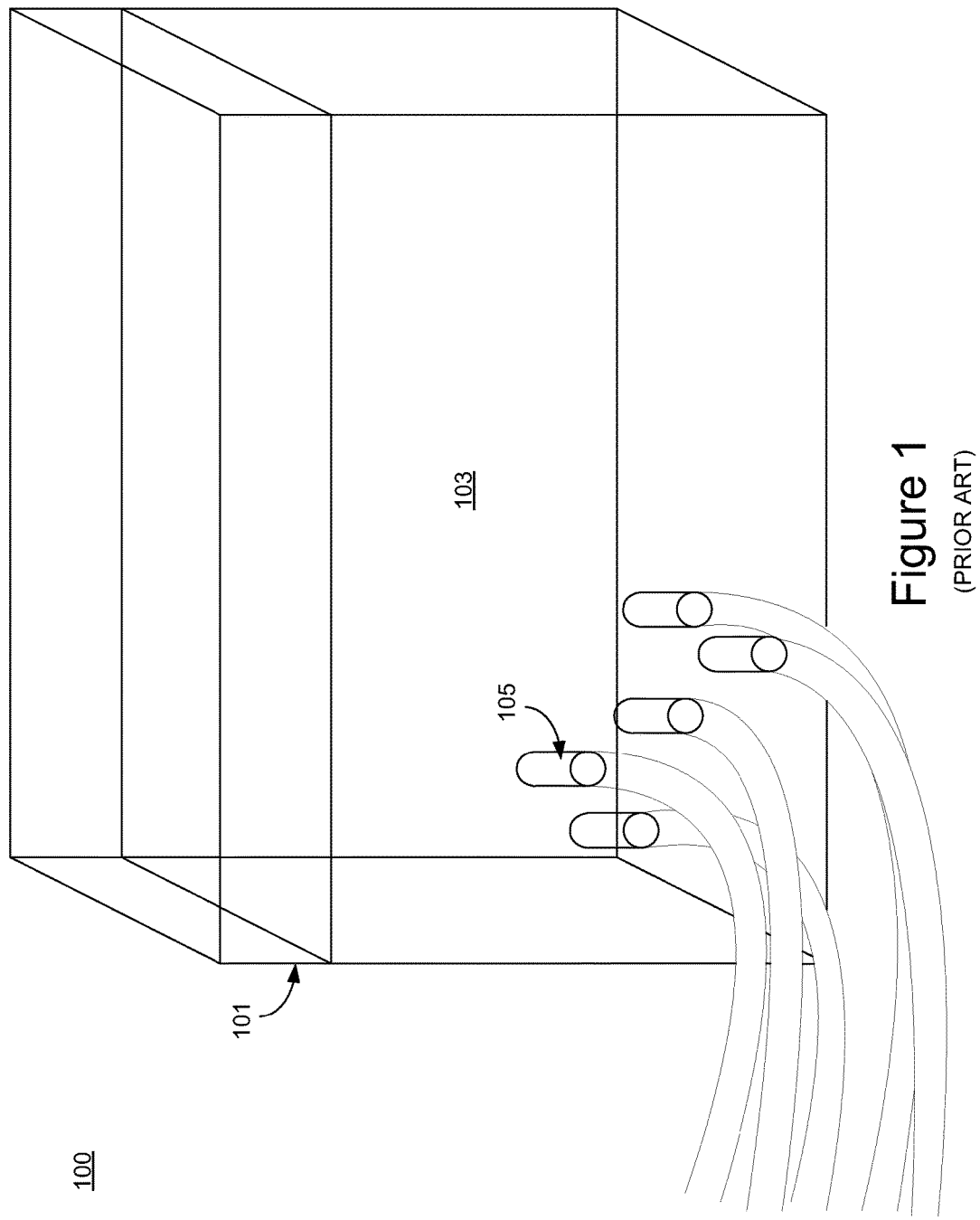
FIG. 1 depicts an illustration of a conventional liquid-state phantom used during maintenance or quality assurance procedures for radiation therapy devices.

With reference now to FIG. 1, an illustration of a conventional liquid-state phantom 100, such as the phantoms typically used during the performance of certain maintenance procedures for radiation therapy devices (such as proton therapy devices) is depicted, in accordance with one embodiment. In one configuration, the liquid-state phantom 100 includes a tank 101 for containing a volume of a liquid 103, and a plurality of radiation monitoring devices 105 submerged or partially submerged within the volume of water 103 and coupled to a detector (not shown) external to the tank 101. Typically, the tank 101 may be comprised of a glass or clear plastic material, and the volume of liquid 103 may consist of, for example, water. In one embodiment, the radiation monitoring devices 105 are arranged such that they do not cause interference during radiation measurements.

A conventional range test may comprise, for example, mounting a liquid-state phantom 100, pumping in a volume of liquid 103 into the phantom 100, generating a beam of irradiated particles in a particle accelerator according to a pre-determined treatment plan, directing a beam of irradiated particles into the liquid-state phantom 100, and receiving the particles in the radiation monitoring devices 105 which are scanned while receiving the proton beam to record the beam's characteristics (e.g., energy at a given range).

However, conventional range determination procedures may require liquid-state phantoms to be of significant size. For example, at 250 MV energy, (a common energy value of a generated proton beam) a proton beam can have a range of up to 38 centimeters. This typically results in usage of liquid-state phantoms which approximate with dimensions of at least 50×50×50 centimeters, with a corresponding volume of water. Naturally, due to the weight of liquid in the tank 101, the phantoms 100 (particularly when filled) may be cumbersome, heavy and/or physically difficult to move and adjust, often requiring two or more operators just to setup the procedure.

Exemplary Solid-State Phantom for Performance of Range Tests

Figure 2:
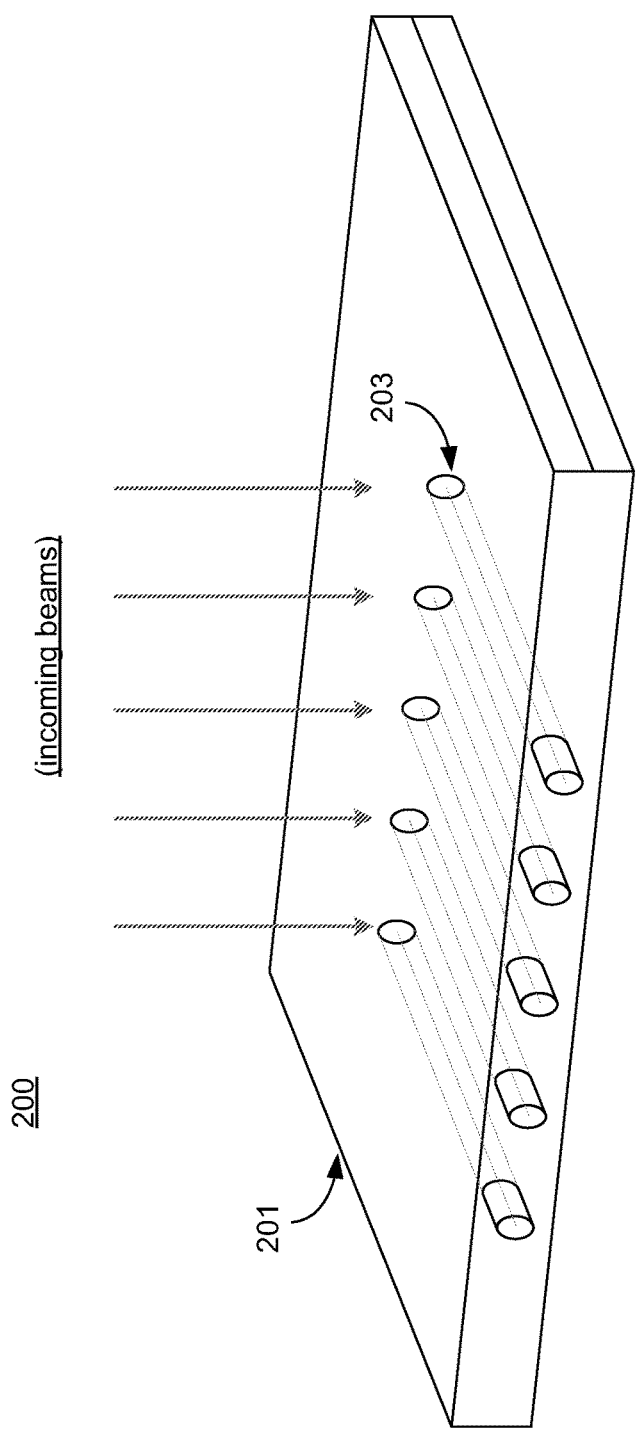
FIG. 2 depicts an illustration of a solid-state phantom comprising a plurality of ionization chambers used during maintenance or quality assurance procedures for radiation therapy devices in accordance with embodiments of the present invention.

According to an embodiment of the present claimed subject matter, quality assurance procedures performed on radiation therapy systems are provided, including a range test for a beam generated by a radiation therapy device that may be performed at regular intervals as part of one or more maintenance procedure(s). With reference now to FIG. 2, a solid-state phantom 200 comprising a plurality of ionization chambers 203 used during maintenance procedures (e.g., a range test) for radiation therapy devices is depicted, in accordance with one embodiment. The solid-state phantom 200 may comprise a solid-state structure 201, a plurality of ionization chambers 203 disposed within the solid-state phantom 200, and a measuring device coupled to the plurality of ionization chambers 203 and operable to perform radiation measurements of proton beams received within the plurality of ionization chambers 203 (not shown). Measurements of proton beam energy received in the ionization chambers 203 may be used to derive the range at the ionization chambers 203, and be subsequently compared to pre-generated target data (e.g., data corresponding to proper treatment according to a radiation therapy treatment plan). If the data obtained through the maintenance procedure does not conform to the target data, the proton beam generator may be further calibrated.

According to one embodiment, the solid state tank 201 may be composed of a plastic or similar, relatively lightweight material, such as Polymethyl methacrylate (PMMA) and may be constructed to be of only a few centimeters in depth. In comparison to conventional, liquid-state phantoms, a solid-state phantom according to embodiments of the present invention will be both lighter and smaller, thereby allowing easier mobility and adjustment, without requiring multiple operators or a water source and drain facilities. As depicted, the solid-state phantom 200 comprises a total of 5 ionization chambers 203, arranged horizontally across a single plane, though embodiments of the present invention are well suited to alternate implementations comprised of a different number of ionization chambers, and/or arrangements. In one embodiment, the ionization chambers 203 are disposed within the solid-state tank 201 at different depths (from the perspective of an oncoming proton beam), and may be used to obtain a set of energies at different angles with respect to the gantry of the generating proton therapy device. The ionization chambers 203 are preferably arranged such that their respective positions within the solid-state tank 201 do not cause interference during energy measurements.

As the ionization chambers are positioned in the solid-state phantom in a rigid state, this novel system allows the performance of maintenance or quality assurance procedures at regular intervals (e.g., daily, weekly, monthly, etc.) to be performed which are insensitive to exact alignment of the phantom with respect to the ionization chambers, as well as makes use of the distal falloff of the Bragg peak of the proton beam by positioning an ionization chamber in the location of the distal falloff, thereby allowing the identification of small drifts in the beam's energy and therefore, efficient calculation of the range of a particle beam.

Exemplary Solid-State Phantom for Performance of Constancy Tests

Figure 3:
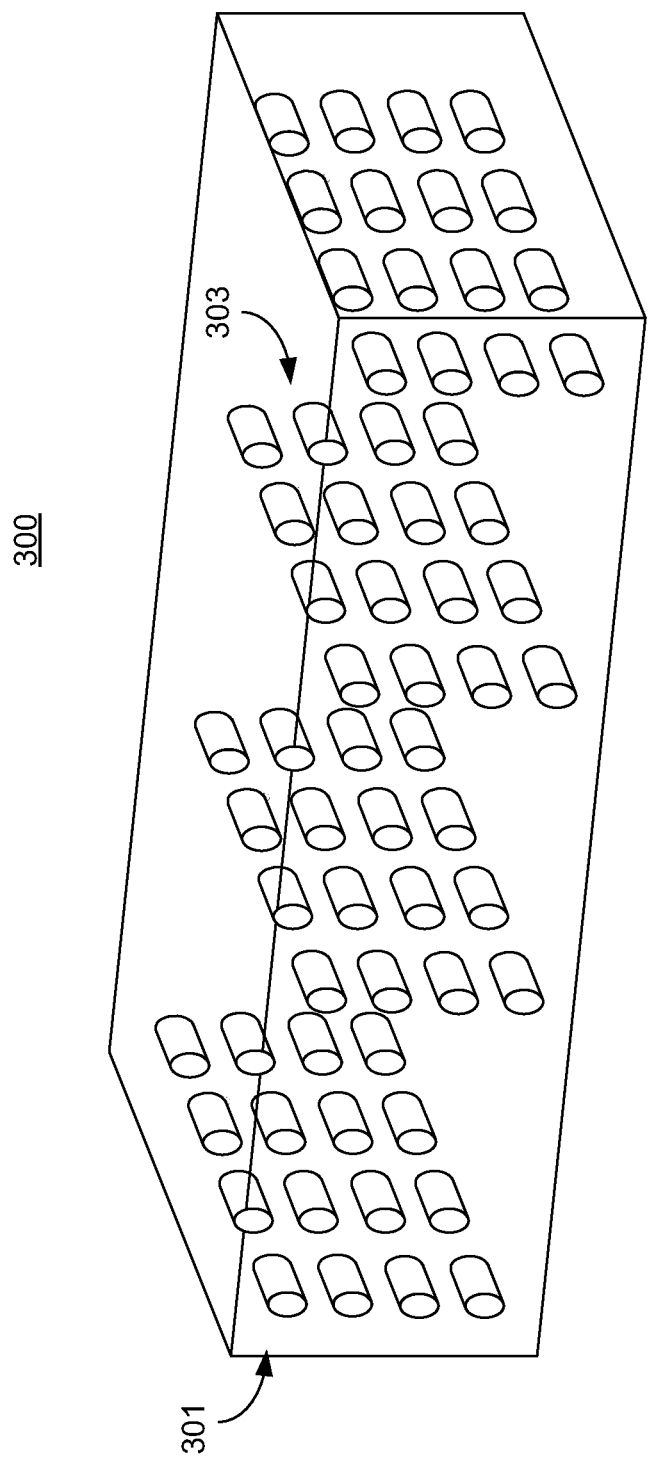
FIG. 3 depicts an illustration of a solid-state phantom comprising a two dimensional array of ionization chambers used during maintenance or quality assurance procedures for radiation therapy devices in accordance with embodiments of the present invention.

With reference now to FIG. 3, a solid-state phantom 300 comprising a two-dimensional matrix of ionization chambers 303 used during maintenance or quality assurance procedures (such as a constancy test) for radiation therapy devices is depicted, in accordance with one embodiment. The solid-state phantom 300 may comprise a solid-state structure 301, and a two-dimensional array of ionization chambers 303 disposed within the solid-state phantom 300. In one embodiment, the two-dimensional array of ionization chambers 303 corresponds to a relatively low resolution (i.e., relatively fewer amount of data points). As shown, a four by four two-dimensional array of ionization chambers 303 is presented for simplicity in FIG. 3. Alternate embodiments may include two-dimensional arrays of different dimensions. For example, a 27 by 27 (729 total) array of ionization chambers may be preferable in some embodiments. Naturally, embodiments are well suited to arrays of various dimensions.

During a constancy test performed with a proton therapy device, a proton beam is generated and applied to a plurality of targeted areas or "spots" on a target or subject in a pre-defined sequence according to a treatment plan for that particular target or subject. In one embodiment, the plurality of targeted spots form a raster comprising portions or all of the two-dimensional array of ionization chambers. Magnetic fields are generated to alter (i.e., by deflecting) the course of the proton beams such that the proton beams are directed to each target spot. Measurements of the absorbed doses deposited by the deflected proton beam and received in the ionization chambers 303 may be used to derive the energy levels of the proton beam at the ionization chambers 303, where the data may be subsequently compared to pre-generated target data (e.g., DICOM data corresponding to proper treatment according to a radiation therapy treatment plan).

If the data obtained through the maintenance or quality assurance procedure does not conform to the target data, the proton beam generator may be further calibrated such that a constant energy is maintained at each spot over the entire treatment field, and according to the radiation therapy treatment plan. Since the resolution of the data obtained over the radiation field is relatively low in comparison to traditional mediums such as film, such a configuration would require a small fraction of the data processing to process a beam treatment sequence. Naturally, this could potentially result in drastic decrease in both time and the amount of processing resources required to perform frequent (e.g., daily) constancy checks of a radiation treatment system.

Figure 4:
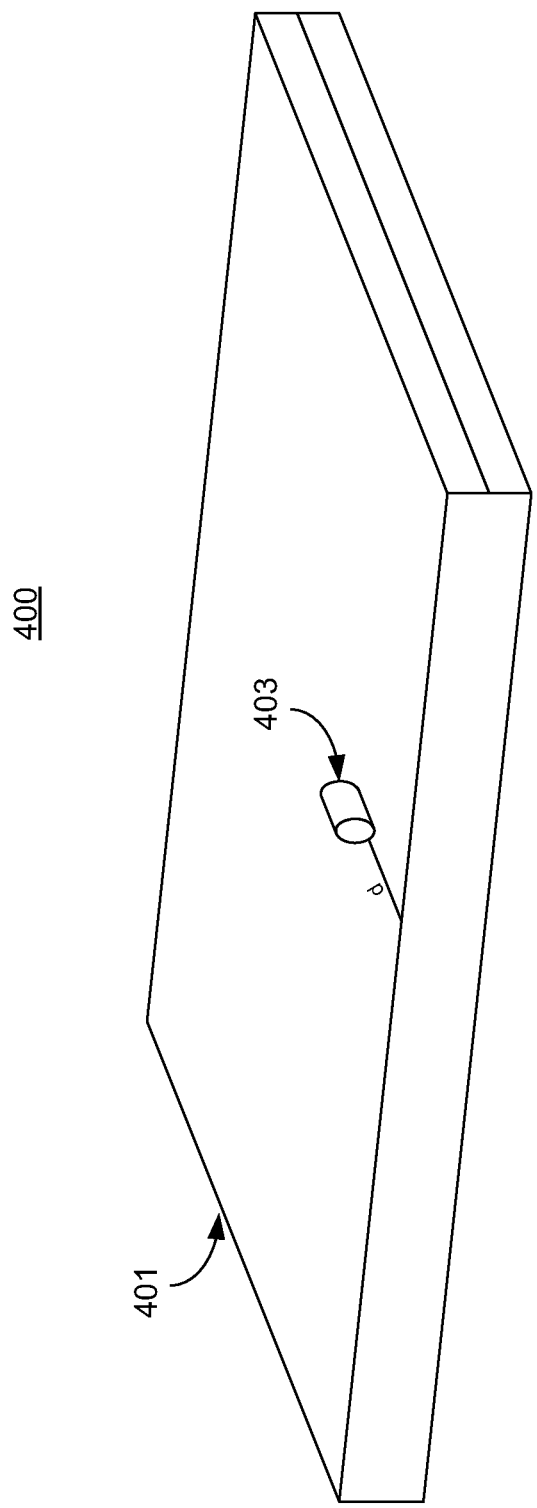
FIG. 4 depicts an illustration of a solid-state phantom comprising a thimble ionization chamber used during maintenance or quality assurance procedures for radiation therapy devices in accordance with embodiments of the present invention.

Exemplary Solid-State Phantom for Performance of Monitor Unit to Dose Calculation With reference now to FIG. 4, a solid-state phantom 400 comprising a single (thimble) ionization chamber 403 used during maintenance or quality assurance procedures (such as dose to monitor unit calculation) for radiation therapy devices is depicted, in accordance with one embodiment. The solid-state phantom 400 may comprise a solid-state structure 401, and a thimble ionization chamber 403 disposed within the solid-state phantom 400 at a shallow depth d (e.g., 1-2 cms). In one embodiment, the solid-state phantom 400 is mounted such that the ionization chamber 403 corresponds to the iso-center of a radiation beam treatment according to a radiation therapy plan.

During a dose to monitor unit calculation test performed with a proton therapy device, a proton beam is generated and applied to a plurality of targeted areas or "spots" on a target or subject in a pre-defined sequence according to a treatment plan for that particular target or subject. During maintenance tests, the target or subject is simulated with a solid-state phantom, such as the phantom 400 depicted in FIG. 4, according to some embodiments. A homogenous, mono-energetic calibration field is generated with pre-defined properties (such as the field size at iso-center, distance between spots, and monitor units per spot). Given the homogenous calibration field, the dose (and, by extension, the absorbed dose amount per number of monitor units) may be measured within the ionization chamber.

The measured dose can be subsequently utilized to normalize (and calibrate) the beam parameters in a treatment plan by comparing the measured dose with expected or target doses. By utilizing this system which incorporates a solid-state phantom, fluence deviations attributable to liquid-state phantoms may be avoided. The shallow calibration depth and homogenous, mono-energetic calibration field avoids dose gradients in a Bragg peak, thereby advantageously providing robust calibration results independent of setup particularities.

Performing a Range Test on Proton Therapy Device

Figure 5:
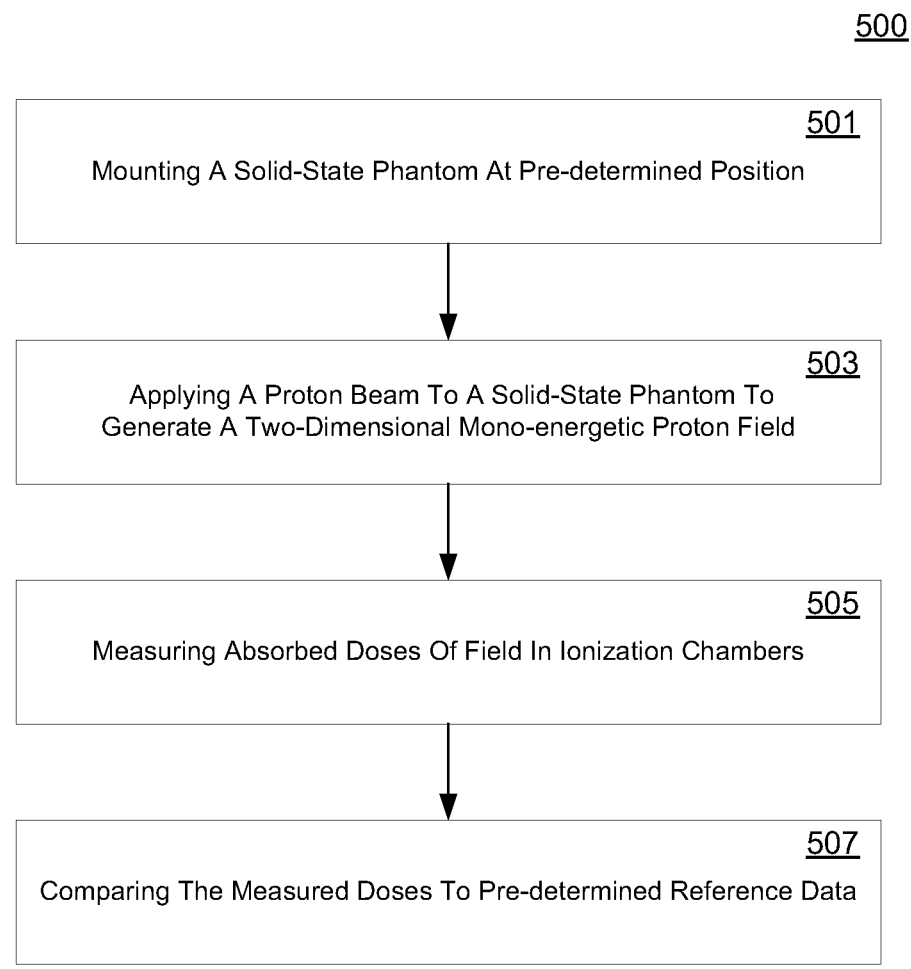
FIG. 5 depicts a flowchart of a method of performing a range test for a proton therapy system during maintenance or quality assurance procedures, in accordance with embodiments of the present invention.

FIG. 5 is a flowchart 500 depicting a method for performing a range test with a solid-state phantom on a radiation therapy device (e.g., a spot scanning proton therapy device), in accordance with one embodiment. Specifically, the method enables the simple and efficient calculation of the range of an emitted radiation beam during a maintenance process of a corresponding radiation therapy device. Steps 501-507 describe exemplary steps comprising the process depicted in flowchart 500 in accordance with the various embodiments herein described. In one embodiment, at least a portion of the steps described flowchart 500 may be performed as computer-executable instructions stored in a computer-readable medium.

At step 501, a solid-state phantom is mounted in a pre-determined position with respect to a proton therapy device. In one embodiment, mounting the solid-state phantom comprises positioning the phantom at a desired distance and/or at a desired angle with respect to a gantry of the proton therapy device. In some embodiments, the solid-state phantom may comprise the plastic or PMMA phantom 200 described above with respect to FIG. 2. At step 503 a proton beam (e.g., a pencil beam) is generated in a particle accelerator and applied to a solid-state phantom to generate a two dimensional mono-energetic field of protons during the performance of a maintenance test. The proton beam may be applied by, for example, generating a beam of protons in a particle accelerator and generating a magnetic field to direct the proton beam to desired targeted positions in the solid-state phantom.

In one embodiment, the desired positions in the solid-state phantom 200 correspond to the positions of the plurality of ionization chambers disposed within the solid-state phantom 200. As the proton beam travels through the solid-state phantom 200, energy (i.e., the "dose" of the proton beam) is deposited in the material of the solid-state phantom 200 along the path of the proton beam. The dose of the proton beam may be measured and recorded within the ionization chambers 203. Thus, the dose of the proton beam at the positions in the field corresponding to the positions of the ionization chambers 203 may be measured and recorded. According to some embodiments, the size of the mono-energetic field of protons generated at step 503 may be substantially equivalent to the volume of the solid-state phantom 200, such that the solid-state phantom 200 may be substantially covered by the mono-energetic field of protons.

At step 505, the doses of the mono-energetic field of protons absorbed by the plurality of ionization chambers 203 within the solid-state phantom 200 are recorded as data. Ionizing radiation (such as radiation from proton beams) experience energy loss as a result of traveling through matter. This energy loss, commonly plotted as a Bragg curve—also exhibits a pronounced peak immediately before the particles come to rest (e.g., where the energy of the particle beam exhibits a significant reduction). This reduction is referred to as the distal falloff the Bragg Peak. For protons, a pronounced peak, called the Bragg peak, is exhibited in a Bragg curve immediately before the protons of a proton beam come to rest, where the energy of the proton beam exhibits a significant reduction (the "distal falloff"). According to some embodiments, the last chamber of the plurality of ionization chambers 203 may be positioned to correspond to the distal falloff the Bragg Peak for a proton beam according to a radiation therapy plan. Accordingly, dose deviations in the remainder of the plurality of ionization chambers 203 may be attributed to deviations from the dose measurement. This eliminates the need to account for the distal falloff when calculating dose which is required by typical range tests, due to the relative lack of mobility of a liquid-state phantom.

At step 507, the measured doses recorded in the plurality of ionization chambers at step 505 may be compared to pre-determined reference data to determine the need for proper (or additional) calibration of the radiation therapy device. In some embodiments, the pre-determined reference data comprises data under the digital imaging and communications in medicine (DICOM) standard. Reference data may comprise plotted data calculated according to a radiation treatment plan. Reference data may also comprise, for example, measured data from previous range tests. By incorporating a solid-state phantom 200, a range test may be performed on a radiation therapy device efficiently and effectively, without requiring multiple operators and while eliminating the need to perform (now) extraneous accounting for distal falloff of the proton beam.

Performing a Constancy Test on Proton Therapy Device

Figure 6:
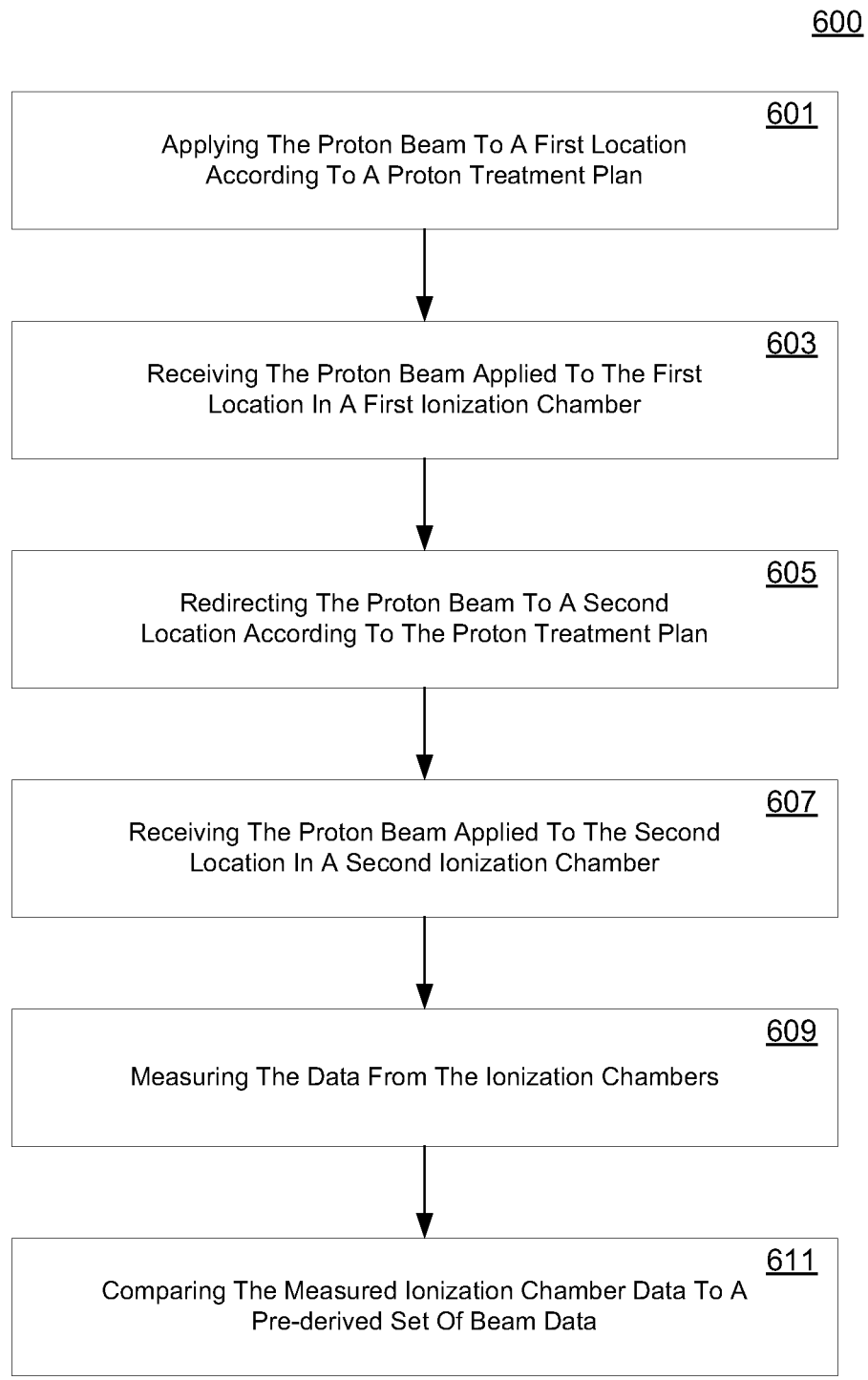
FIG. 6 depicts a flowchart of a method of performing a constancy test for a proton therapy system during maintenance or quality assurance procedures, in accordance with embodiments of the present invention.

FIG. 6 is a flowchart 600 depicting a method for efficiently performing a constancy test with a solid-state phantom on a radiation therapy device (e.g., a spot scanning proton therapy device), in accordance with one embodiment. Specifically, the method enables the simple and efficient calculation of the constancy of a homogenous flux of radiation generated at a target from a radiation beam emitted during a maintenance process of a corresponding radiation therapy device. Steps 601-611 describe exemplary steps comprising the process depicted in flowchart 600 in accordance with the various embodiments herein described. In one embodiment, at least a portion of the steps described flowchart 600 may be performed as computer-executable instructions stored in a computer-readable medium.

At step 601, a proton beam (such as a pencil beam) is applied to a two-dimensional array of ionization chambers 303 during a maintenance or quality assurance test. In one embodiment, the pencil beam may be applied to a plurality of positions corresponding to individual ionization chambers within the two-dimensional array of ionization chambers 303. These positions may correspond to the planned treatment spots of a treatment plan (or pre-defined test plan). According to some embodiments, the two-dimensional array of ionization chambers 303 may be disposed in a solid-state phantom 301 (e.g., the solid-state phantom 300 described above with respect to FIG. 3), mounted in a pre-determined position with respect to a proton therapy device. According to one embodiment, the dimensions of the solid-state phantom 301 may correspond to the dimensions of conventional, liquid containing phantoms. According to further embodiments, the solid-state phantom 301 may be any size suitable to contain the two-dimensional array of ionization chambers 303.

In one embodiment, the two-dimensional array of ionization chambers 303 may comprise a 27 by 27 arrangement (729 total single ionization chambers) of single ion chambers separated from each other by, for example, a distance of approximately one centimeter, thereby providing a relatively low-resolution apparatus capable of measuring the dose of the pencil beam over a larger volume. Naturally, embodiments are well suited to other arrangements, and in particular, to arrangements maintaining low-resolution/wide volume coverage. As with the solid-state phantom used in the range test described above with respect to FIG. 4, the solid-state phantom may also be constructed from plastic or PMMA.

At step 603 the proton beam generated and applied at 601 is received in a first location in the solid-state phantom 301 according to a pre-determined treatment plan (or pre-defined test plan) and corresponding to a first ionization chamber in the two-dimensional array of ionization chambers 303. At step 605, the proton beam is redirected to a second location in the solid-state phantom 301 corresponding to a second ionization chamber of the two-dimensional array of ionization chambers 303 where it is received at step 607. The second location may, for example, correspond to the next target spot in a sequence of target spots according to the pre-determined treatment plan. In one embodiment, the proton beam is directed by generating a magnetic field through a current at the treatment head of the radiation therapy device. Redirection of the proton beam performed at step 605 may be performed by altering the magnetic field to influence the path of the emitted proton beam. Steps 603 to 607 may be repeated for additional spots according to the treatment plan.

At step 609, the doses deposited by the pencil beam within the ionization chambers of the two-dimensional array of ionization chambers 303 during execution of the treatment plan are recorded and measured. At step 611, the measured doses recorded in the two-dimensional array of ionization chambers 303 at step 609 may be compared to pre-determined reference data to determine the need for proper (or additional) calibration of the radiation therapy device. In some embodiments, the pre-determined reference data comprises data under the digital imaging and communications in medicine (DICOM) standard. Reference data may comprise plotted data calculated according to a radiation treatment plan. Reference data may also comprise, for example, measured data from previous constancy tests. By incorporating two-dimensional array of ionization chambers with a relatively low-resolution in a solid-state phantom 200, a constancy test may be performed on a radiation therapy device efficiently and effectively, without requiring multiple operators and while drastically reducing the amount of processing required for conventional constancy tests conducted over traditional mediums.

Performing Monitor Unit to Dose Calibration

Figure 7:
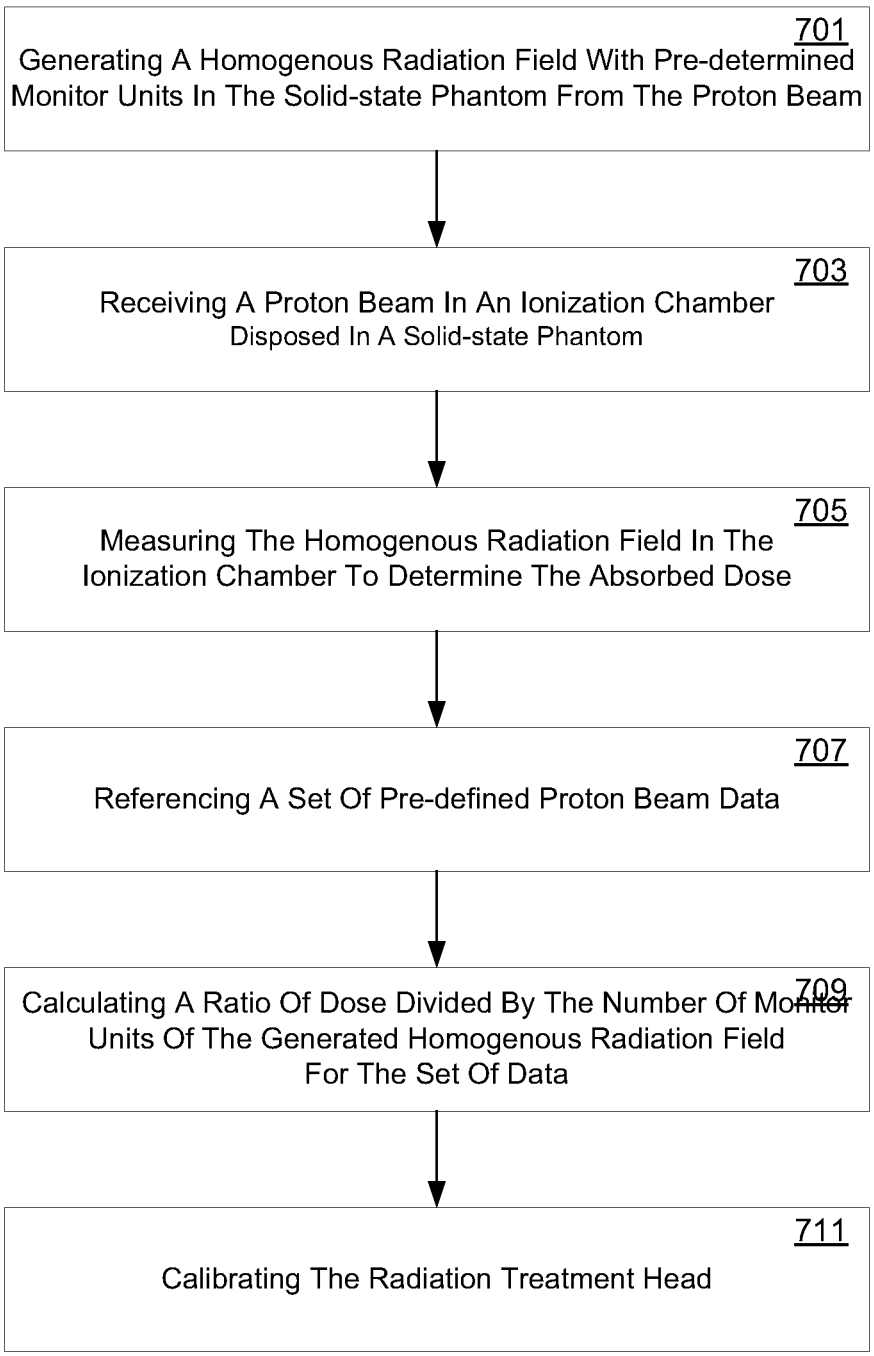
FIG. 7 depicts a flowchart of a method of performing a calibration of a proton therapy system based on a calculated radiation dose performed during maintenance or quality assurance procedures, in accordance with embodiments of the present invention.

FIG. 7 is a flowchart 700 depicting a method for efficiently performing a calculation of dose generated from measurements of detected monitor units observed during the course of a radiation therapy treatment. This therapy may include, for example, proton spot scanning treatments which apply a pencil beam of protons to a plurality of target spots distributed over a target treatment area. When the proton beam is received in an ionization chamber, such as during maintenance or quality assurance tests, the air in the dose monitor chambers of the radiation treatment head through which the proton beam passes become ionized with energy (the dose of the proton beam). The ionized air creates charges known as "monitor units" which can be measured and recorded, from which a dose corresponding to the proton beam may be subsequently derived. Steps 701-711 describe exemplary steps comprising the process depicted in flowchart 700 in accordance with the various embodiments herein described. In one embodiment, at least a portion of the steps described flowchart 700 may be performed as computer-executable instructions stored in a computer-readable medium.

At step 701, a proton beam (such as a pencil beam) is generated during a maintenance or quality assurance test. At step 703, the generated proton beam is received in a calibrated ionization chamber disposed in a solid state phantom. In one embodiment, the proton beam comprises a pencil beam generated from a proton therapy device, and the ionization chamber comprises a thimble ionization chamber disposed at a relatively shallow (approximately 1-2 cm) depth in the solid state phantom, such as the solid-state phantom 400 described above with respect to FIG. 4. In further embodiments, the phantom 400 may be mounted at a pre-determined position such that the position of the thimble ionization chamber 403 corresponds to the iso-center of a radiation therapy treatment plan. According to still further embodiments, the pencil beam may be applied to a plurality of positions within or about the phantom 400 to generate a homogenous radiation field. The homogenous radiation field may be generated with pre-determined characteristics, such as the field size at the iso-center, number of spots, the distance between spots, and monitor units per spot, etc. In further embodiments, the homogenous radiation field generated is a mono-energetic, two-dimensional radiation field.

The homogenous radiation field is measured at 705 and compared to a set of pre-defined proton beam data at step 707 to determine the dose absorbed in the thimble ionization chamber 403 during the maintenance or quality assurance test. Given the pre-determined characteristics of the generated homogenous radiation field, the dose may be calculated at step 709 by, for example, comparing the absorbed dose observed in step 705 at the thimble ionization chamber 403 during the test with the pre-determined beam field characteristics referenced at step 707. According to one embodiment, calculating the dose may be performed by, for example, deriving the ratio from dividing the dose by the number of monitor units of the homogenous radiation field generated in step 701 for each data point in the set of data. Finally, at step 711, the dose measured in step 709 can be subsequently utilized to normalize (and calibrate) the parameters of the proton beam in a treatment plan by comparing the measured dose with expected or desired doses.

As described herein, systems and methods for performing daily maintenance or quality assurance of a proton therapy system which drastically reduce the difficult and/or complexity of conventional daily maintenance or quality assurance tests. In particular, the usage of a solid-state phantom to replace traditional liquid-state phantoms eliminate a significant portion of user effort required to even set up maintenance tests for range, constancy, and dose calculation, while providing robust measurements independent of set up errors. Likewise, the utilization of a two-dimensional array of ionization chambers to record data drastically reduces the processing required to perform a constancy test over traditional methods.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system comprising:
a solid-state phantom;
a plurality of ionization chambers disposed inside the solid-state phantom; and
a measuring device coupled to the plurality of ionization chambers and operable to measure radiation in the plurality of ionization chambers of a plurality of charged air particles produced from a passage of a proton beam through at least one ionization chamber of the plurality of ionization chambers, wherein the plurality of ionization chambers comprises an ionization chamber that is furthest from a source of the proton beam, relative to the others of the ionization chambers, at a position in the phantom at a depth, relative to the direction of the proton beam, that corresponds to a position of the distal falloff of a Bragg peak for the radiation measured by the measuring device;
wherein a radiation generating device comprises the source of the proton beam,
further wherein a plurality of charged air particles produced from a passage of the proton beam through at least one ionization chamber of the plurality of ionization chambers is expressed in a number of monitor units measured by the measuring device to perform a constancy check of the radiation generating device.

2. The system according to claim 1, wherein the proton beam generated by the radiation generating device generates a mono-energetic field of protons targeted at the solid-state phantom.

3. The system according to claim 1, wherein the measuring device comprises a multi-channel electrometer.

4. The system according to claim 1, wherein the constancy check comprises receiving the proton beam in the plurality of ionization chambers at a plurality of different angles.

5. The system according to claim 1, wherein the phantom is comprised of plastic.

6. The system according to claim 1, wherein the phantom is comprised of at least one of: polymethyl methacrylate (PMMA) and polycarbonate.

7. The system according to claim 1, wherein the measuring device measures doses of radiation from protons of the proton beam that are received in the plurality of ionization chambers.

8. The system according to claim 1, wherein the constancy check of the radiation generating device comprises determining the range of the proton beam generated by the radiation generating device from the distal falloff of the Bragg-peak curve corresponding to the radiation measured by the measuring device.

9. The system according to claim 1, wherein the plurality of ionization chambers comprises ionization chambers arrayed in a matrix configuration in the solid-state phantom.

10. The system according to claim 1, wherein the plurality of ionization chambers comprise an ionization chamber that is a thimble ionization chamber.

11. The system according to claim 1, wherein the plurality of ionization chambers comprise an ionization chamber that is disposed within the solid-state phantom at a shallow depth relative to the direction of the proton beam.

12. The system according to claim 1, wherein the proton beam is directed at the plurality of ionization chambers in a predefined sequence according to a radiation plan.

13. The system according to claim 1, wherein the number of monitor units is measured and recorded, and wherein a radiation dose is derived from the number.

* * * * *